United States Patent [19]

Seilinger

[11] Patent Number: 4,643,183
[45] Date of Patent: Feb. 17, 1987

[54] APPARATUS FOR PRODUCING HOT AIR FOR INHALATIONS

[76] Inventor: Alexandre Seilinger, 2, Square de la Baume Rocquencourt, 78150 Le Chesnay, France

[21] Appl. No.: 716,482

[22] Filed: Mar. 27, 1985

[30] Foreign Application Priority Data

Mar. 27, 1984 [FR] France ............... 84 04742

[51] Int. Cl.⁴ ............................................. A61M 15/00
[52] U.S. Cl. ........................... 128/204.17; 128/205.11; 128/205.24; 128/207.13
[58] Field of Search ................. 128/204.17, 203.27, 128/203.26, 203.22, 203.28, 205.11, 205.24, 203.29, 207.13

[56] References Cited

U.S. PATENT DOCUMENTS

| 731,973 | 6/1903 | Teter | 128/207.13 |
| 743,294 | 11/1903 | Knowles | 128/203.28 |
| 1,151,649 | 8/1915 | Barr | 128/203.27 |
| 1,202,877 | 10/1916 | Morgan | 128/203.29 |
| 2,091,034 | 8/1937 | Duncan | 128/203.27 |
| 3,045,670 | 7/1962 | Hirtz et al. | 128/203.27 |
| 3,115,134 | 12/1963 | Schmahl | 128/203.29 |
| 3,139,885 | 7/1964 | Hirtz et al. | 128/203.27 |
| 3,881,480 | 5/1975 | Lafourcade | 128/205.24 |
| 3,985,131 | 10/1976 | Buck et al. | 128/205.24 |
| 4,437,461 | 3/1984 | Greenberg | 128/205.24 |

Primary Examiner—Henry J. Recla
Attorney, Agent, or Firm—Martin P. Hoffman; Mitchell B. Wasson; Charles W. Fallow

[57] ABSTRACT

Apparatus for producing hot air for inhalations at stabilized pressure and temperature, comprising a source delivering air at a constant pressure, an electric resistor in contact with that air under pressure, an intermediate chamber receiving all of the hot air and opened to atmosphere in adjustable manner, and an inhaling device (e.g. a mask), said intermediate chamber being in communication with the inhaling device (4) through means (11-12) limiting to the hot-air flow rate into said device to a minute value with respect to the flow exhausted to atmosphere.

6 Claims, 3 Drawing Figures

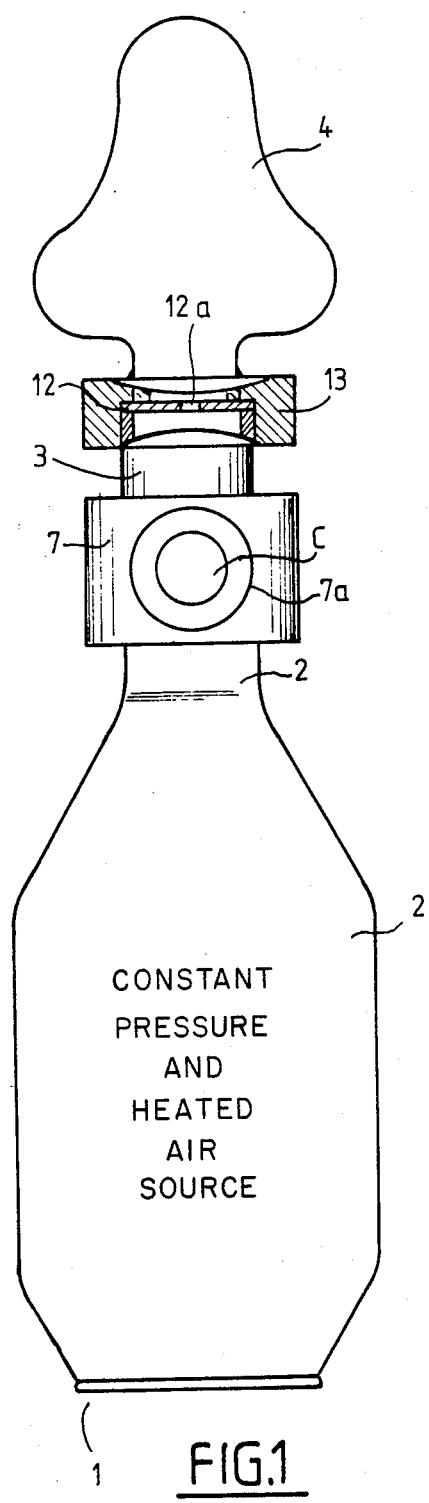
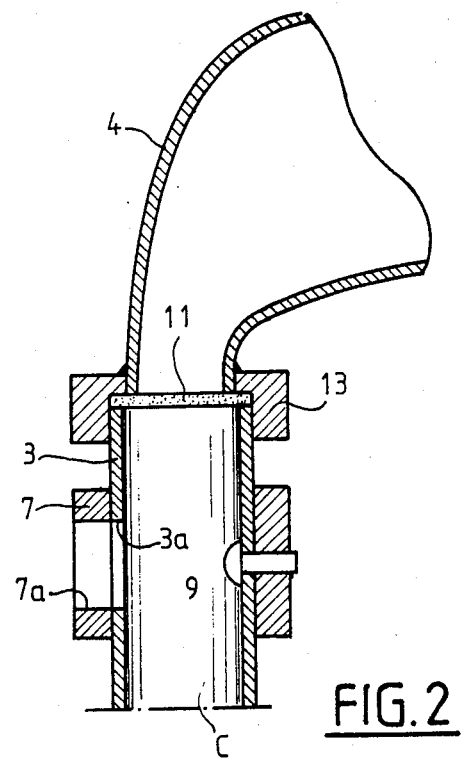
FIG.2
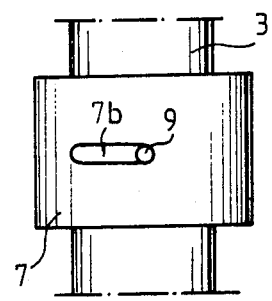
FIG.3
FIG.1
CONSTANT PRESSURE AND HEATED AIR SOURCE

4,643,183

APPARATUS FOR PRODUCING HOT AIR FOR INHALATIONS

FIELD OF THE INVENTION

This invention relates to an apparatus for producing hot air for inhalations.

THE PRIOR ART

It is well known that air heated to a sufficiently high temperature permits treatment of viral rhinitis, agents of which badly develop above 360° C., and of allergic rhinitis according to an imperfectly cleared-up process.

There are on the market a number of apparatus of inhaler type including a blower directing air onto an electric resistor, wherein all of heated air flow is directed towards a bucconasal mask (e.g., FR-A No. 1 083 197), such apparatus being more or less offered as medical ones (FR-A No. 1 555 598). It has been ascertained that these apparatus do not satisfy the respiratory needs of patients, the volume of hot air delivered being too high, which results in a kind of suffocation, of which user of the apparatus can get rid only by keeping away the mask resulting in entering cold air. Thus, there has been suggested devices for suppressing a part of that hot air.

According to U.S.-A No. 2 091 034 is it provided to put at the vicinity of the buccal part for inhalation output derivations which according to that patent are deemed to eliminate the non inhaled air in excess. Obviously that is the entire flow which reaches the patient and that air in excess can only be eliminated through a flow-back owing to breathing out thereof. CH-A No. 381 362 suggests to provide the chamber receiving hot-air flow on the one hand with a valve and on the other hand with communicating means to open air, the valve acting as a pressure regulator and the communicating means to open air acting as a regulating means both for pressure and temperature.

The problem becomes complicated when practitioners noted that it is not sufficiant to deliver to the patient hot air, but it is required that same be at a stabilized pressure and temperature whatever volume is consumed.

Owing to that observation manufacturers conceived apparatus in which hot-air production is acted on by means of quite complicated and expensive regulators frequently without reaching the intended object.

Really it appears that a stabilized pressure cannot be effectively reached if both of inspiration and expiration flows join together.

This explains the reaction why the apparatus set forth in the patents U.S.-A No. 2 091 034 and CH-A No. 381 362 have to be considered as ineffective—they lack means for dividing the air volume so as to obtain a flow to be inhaled at a stabilized pressure.

SUMMARY OF THE INVENTION

This invention relates to an apparatus for producing hot air for medical use, comprising a device able to furnish in a very simple and quite economical manner pulsed hot air at stabilized pressure and temperature.

The principle of the apparatus is to provide in large quantity hot air and to only use a very small quantity for the sake of treatment.

To reach that result in an economical manner in an apparatus comprising three essential parts a hot-air generator including a source delivering air at a constant pressure (e.g., an air blower) and an electric resistor in contact with that air under pressure.

an intermediate chamber receiving all of the hot air and opened to atmosphere in an adjustable manner, a utilisation chamber (e.g. a mask), there is provided between the intermediate chamber and the utilisation chamber means for limiting the input flow rate of hot air in latter chamber to a minute value with respect to the hot-air flow evacuated to atmosphere.

Other particularities and advantages become evident at reading of the disclosure and of the subsequent claims drafted with regard to the accompanying drawings, wherein:

THE DRAWINGS

FIG. 1 is an elevation view of an implementation of the apparatus on the side opposite with respect to the patient's face;

FIG. 2 is a partial sectional view taken along 2—2 of FIG. 1;

FIG. 3 is a partial elevation view on the side towards the patient's face.

DESCRIPTION OF THE PREFERRED EMBODIMENT

According to an embodiment illustrated as a non limitating example, as seen on that figures the apparatus 1 for producing hot air of the invention includes on one hand in a housing 1, a hot-air generator 2 constituted of a source delivering air under pressure, by example an electric air blower, and of an electric resistor and on the other hand a tubular body 3 and an inhaling device 4—shown as a nasal mask. The air blower could obviously be replaced with an other sort of source delivering an air under pressure, e.g. an air circuit of the type used in hospital centers. Likewise the nasal mask could be replaced with injection nozzles to be either introduced into the nose or disposed under the patient's nose.

The tubular body 3 communicating on the one hand with the generator 2 and on the other hand with the inhaling device 4 is arranged in the form of an intermediate chamber receiving the totality of the produced hot-air flow.

That intermediate chamber C is put in communication to atmosphere through an adjustable device. To that end the wall of the tubular body is perforated with an opening 3a which can be more or less closed by a movable shutter consisting of a sleeve 7 having therethrough at least an opening 7a (or a plurality of openings with different cross-sections).

Regulating is operated by rotating the sleeve 7 so as to put more or less openings 3a and 7a in registration. A pin 9 fixedly secured on the body 3 and circulating through an elongated slot 7b of the sleeve 7 limits movement thereof with respect to the hollow body, by being inserted in an elongated slot 10 in said sleeve. When the pin 9 as shown on the three figures is abutting against an end of the slot 7b, axis of the openings 3a and 7a coincide and the section for evacuating air is then a maximum one. If the sleeve 7 is rotated, the opening 3a is partially closed and when the other end of the slot 7b is placed in abutting relation against the pin 9, the section for evacuating hot air is minimum.

The intermediate chamber C provided in the tubular body 3 is in communication with the inhaling device by means of an aperture 4a through a flow rate regulating member essential to the invention.

As previously recited, the principle of the apparatus consists in drawing out of the total flow only a minute part thereof for inhalation. Otherwise that flow rate regulating member, in which pressure loss is known, allow a residual pressure and a stabilized temperature to be established in the inhaling device, i.e. the nasal mask 4.

As seen on FIG. 1 communication between the chamber C and the mask is created through a diaphragm 12 made up with a cap having therethrough a calibrated hole 12a disposed through the drawing out opening 4a.

The diaphragm with calibrated hole could be replaced with devices having same function of regulating the flow rate.

Said devices could be either a filter or a cartridge 11 (FIG. 2) containing medicinal products able to evaporate or sublimate. By giving that filter (on that cartridge) a usable section allowing to draw out air in the intermediate chamber.

It is obvious to understand that the usable section for the transit of air through the calibrated hole 12a or through a filter or a cartridge 11 having a controlled pressure loss is very small with respect to the section of the opening 3a for exhausting the principal hot-air flow, even when said opening is partially closed by the sleeve 7. The diaphragm 12 or the cartridge 11 is maintained in position by a ring 13, on which a mask 4 is affixed by welding, said mask being provided for covering the patient's nose, but not the mouth.

The characteristics of generator 2 being constant and the opening being completely open, constant temperature and pressure are achieved in the chamber whatever the air quantity consumed by the patient is. Rotating the sleeve 7 so as to partially close the opening 3a results in a drop of the output air flow rate of the principal flow, which in turn results in increasing temperature and pressure in the chamber C; a unique temperature and a unique pressure independent of the consummated air correspond to each position of the ring 7.

Modifications can be made to the apparatus depending on desired special results.

By way of example it could be interesting to filter air without the filter constituting the opening having a small usable section allowing the drawing out of air of the intermediate chamber. In that case it could be disposed either on the level of the opening used for drawing off outdoor air or between the hot-air generator and the intermediate chamber.

The apparatus also allows to inhale humid air. Then it is only necessary either to replace the cartridge disclosed above with a water evaporator supplied or not through a small appended tank or to allow water steam delivered by an external generator to penetrate into the inhaling device through a suitable opening.

Otherwise with the generator producing an essentially constant increase of temperature of the surrounding air, it can be necessary to modify that temperature increase if the surrounding air is not at a normal temperature of 19°/20° C.

Finally if it is possible to use a plurality of different types of inhalers, filters, or cartridges with the same assembly including the hot-air generator and the intermediate chamber, it can be necessary to dispose of the air temperature range of the air in said intermediate chamber particularly for taking into account calories taken up either by the evaporation of water or by the evaporation or sublimation of medicinal products.

All that problems are resolved by means of the capacity of regulation of the output 3 by acting on the sleeve 7, a ring mounted around the intermediate chamber allowing to control the flow rate of air which exhausts through the big opening by closing it more or less and so to reach in the intermediate chamber C the air temperature necessary for the inhaled air to be at the desired temperature. It is to be noted that the regulating means 11-12 permit to obtain inside of the inhaler device a pressure slightly above the patient's expiration pressure.

What is claimed is:

1. An apparatus for producing heated air for therapeutic purposes at stabilized pressure and temperature comprising a source for delivering air at a constant pressure; means for heating said air under pressure; an intermediate chamber in communication with said source including means for receiving all of the heated air; movable shutter means by which said intermediate chamber communicates with the atmosphere, said shutter means being adapted to selectively exhaust said heated air into the atmosphere whereby the pressure and temperature of said heated air in said intermediate chamber is regulated; an inhaling device connected to said intermediate chamber and flow limiting means disposed between said intermediate chamber and said inhaling device, said flow limiting means being adapted to limit the flow of said heated air from said intermediate chamber into said inhaling device to a minute value with respect to the heated air flow exhausted into the atmosphere.

2. An apparatus according to claim 1 wherein said adjustable device comprises a first opening in a side wall of said intermediate chamber and a second opening in a ring rotatably mounted on said intermediate chamber such that said first and second openings can be aligned upon rotation of said ring.

3. An apparatus according to claim 2 wherein an outwardly extending pin member is provided on said intermediate chamber, said pin member being received within an elongated radial slot in said ring whereby the rotational movement of said ring is limited.

4. An apparatus according to claim 1 wherein said limiting means limits said heated air flow into said inhaling device such that said heated air is at a pressure slightly above the expiration pressure of the patient.

5. An apparatus according to claim 1 wherein said inhaling device is a nasal mask.

6. An apparatus according to claim 1 wherein said flow limiting means is adapted to contain a medicament.

* * * * *